United States Patent [19]

Buckley et al.

[11] Patent Number: 4,738,675
[45] Date of Patent: Apr. 19, 1988

[54] DISPOSABLE DIAPER

[75] Inventors: Mary E. Buckley, Wheeling, Ill.; Hamzeh Karami, Walpole, Mass.

[73] Assignee: The Kendall Company, Boston, Mass.

[21] Appl. No.: 11,650

[22] Filed: Feb. 6, 1987

[51] Int. Cl.⁴ .............................................. A61F 13/16
[52] U.S. Cl. .................................................... 604/380
[58] Field of Search ...................... 604/379, 380, 385.1, 604/385.2

[56] References Cited

U.S. PATENT DOCUMENTS

| | | | |
|---|---|---|---|
| 2,890,700 | 6/1959 | Holm | 604/380 X |
| 3,993,820 | 11/1976 | Repke | 604/380 X |
| 4,213,459 | 7/1980 | Sigl et al. | 604/380 |
| 4,336,803 | 6/1982 | Repke | 604/385.2 |
| 4,443,512 | 4/1984 | Delvaux. | |
| 4,461,621 | 7/1984 | Karami et al. | |
| 4,496,358 | 1/1985 | Karami et al. | 604/379 |

FOREIGN PATENT DOCUMENTS 1547524 6/1979 United Kingdom.

Primary Examiner—John D. Yasko
Attorney, Agent, or Firm—Powell L. Sprunger

[57] ABSTRACT

A disposable diaper comprising, a fluid impervious back sheet, a fluid pervious front sheet, a first absorbent pad adjacent the front sheet and comprising a loosely formed fibrous mass, and a separate second absorbent pad between the first pad and the back sheet, with the second pad comprising a mass of fibers having compressed regions extending throughout a substantial part of the second pad and having relatively uncompressed areas adjacent the regions, with the regions being spaced from opposed side edges of the second pad.

14 Claims, 1 Drawing Sheet

DISPOSABLE DIAPER

BACKGROUND OF THE INVENTION

The present invention relates to disposable diapers.

During the past few years, the number of adults with incontinence and are using adult diapers or briefs to deal with the problem has increased dramatically. Many adults are using disposable diapers although there are complaints associated with their use. In particular, the diapers are bulky, and, because their crotch width to overall length ratio is much smaller than that of baby diapers, they tend to become weak when wet and fall apart or bunch up in the crotch area. In addition, because the overall length of the diaper is so large, fluid tends to pool in the crotch area rather than being transferred to the ends of the diaper.

SUMMARY OF THE INVENTION

A principal feature of the present invention is the provision of an improved disposable diaper.

The disposable diaper of the present invention comprises, a fluid impervious back sheet, a fluid pervious front sheet, a first absorbent pad adjacent to the front sheet and comprising a loosely formed fibrous mass, and a separate second absorbent pad between the first pad and the back sheet, with the second pad comprising a mass of fibers having compressed regions extending throughout a substantial part of the second pad and having relatively uncompressed areas adjacent the regions.

A feature of present invention is that the regions are spaced from opposed side edges of the second pad.

Another feature of the invention is that the spacing of the regions from the side edges of the second pad minimizes spreading of fluid along the side edges of the second pad.

A further feature of the present invention is that the compressed regions provide for spreading of fluid adjacent to the back sheet.

Yet another feature of the present invention is that the regions add strength to the crotch region of the pad which otherwise might bulk up during use.

In a preferred form, the diaper is designed for use with adults, and thus have relatively long pads. The regions preferably comprise a plurality of generally parallel spaced lines extending between opposed end edges of the second pad. Also, in a preferred form, the diaper has elastic members adjacent the side edges of the pads in the crotch region of the diaper.

Another feature of the present invention is that the regions transmit fluids to the ends of the pad particularly against the force of gravity.

Thus, the second pad of the present invention prevents pooling of fluid in the crotch region of the diaper.

Yet another feature of the invention is that spacing of the regions from the side edges provides a cushion for the wearer when used in conjunction with the elastic members.

Further features will become more fully apparent in the following description of the embodiments of this invention and from the appended claims.

DESCRIPTION OF THE PREFERRED EMBODIMENTS

Figure 1:
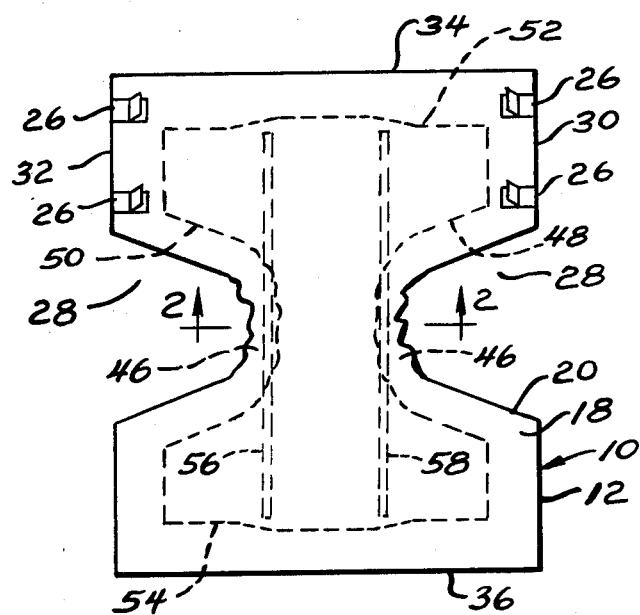
FIG. 1 is a front plan view of a disposable diaper of the present invention.
Figure 2:
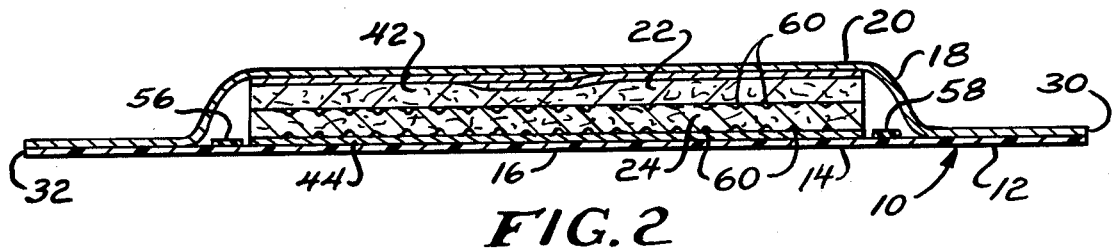
FIG. 2 is a sectional view taken substantially as indicated along the line 2—2 of FIG. 1.
Figure 3:
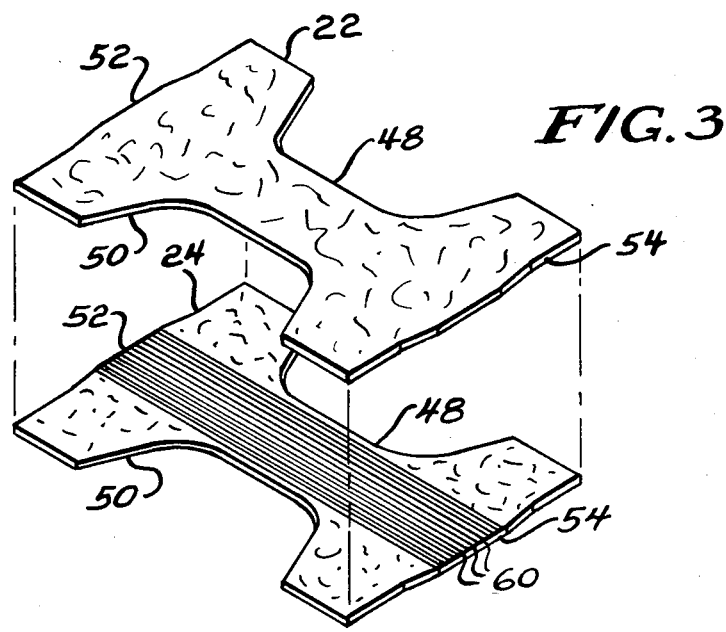
FIG. 3 is an exploded perspective view of first and second absorbent pads for the diaper of FIG. 1.

Referring now to FIGS. 1-3, there is shown a disposable diaper generally designated 10 which is preferably used by incontinent adults, and has a substantially greater length than width in the crotch region of the diaper. The diaper 10 comprises an absorbent pad assembly 12 having a fluid impervious backing sheet 14, such as polyethylene, defining a back surface 16 of the pad assembly 12, a fluid pervious cover or front sheet 18, such as a non-woven material, defining a front surface 20 of the pad assembly 12, and a pair of first and second absorbent pads 22 and 24 between the backing sheet 14 and the front sheet 18. The pad assembly 12 has a pair of tape fasteners 26 in a waistband along each side of conventional type for securing the diaper about a wearer. As shown, the pad assembly 12 has a pair of cut-outs 28 in the crotch region of the pad assembly 12.

The pad assembly 12 has a pair of opposed side edges 30 and 32 extending along sides of the absorbent pad assembly 12, and a pair of opposed end edges 34 and 36 connecting the side edges 30 and 32. The front sheet 18 is secured to the backing sheet 14 by suitable adhesive along the side edges 30 and 32 and adjacent the end edges 34 and 36.

The first pad 22 is located adjacent the front sheet 18, and the second pad 24 is located intermediate the first pad 22 and the backing sheet 14. In a preferred form, the pad assembly 12 has a front wadding sheet 42 located intermediate the first pad 22 and the front sheet 18, and a back wadding sheet 44 located intermediate the second pad 24 and the backing sheet 14. The first and second pads 22 and 24 also have cut-outs 46 in the crotch region of the pad assembly 12. The first and second pads 22 and 24 have a pair of opposed side edges 48 and 50, and a pair of opposed end edges 52 and 54 connecting the side edges 48 and 50. As shown, the side edges 48 and 50 and the end edges 52 and 54 of the first and second pads 22 and 24 are spaced from the side edges 30 and 32 and the end edges 34 and 36 of the pad assembly 12. In a preferred form, the pad assembly 12 has a pair of opposed elastic members 56 and 58 secured to the backing sheet 14 and extending along the opposed side edges 48 and 50 of the first and second pads 22 and 24 in the crotch region of the diaper, with end portions of the elastic members 56 and 58 being located beneath the second pad 24 on opposed sides of the crotch region.

The first absorbent pad 22 comprises a loosely formed fibrous mass, such as wood fluff. However, the second pad 24 comprises a mass of fibers, such as wood fluff, having a plurality of generally parallel lines 60 of compressed regions or embossing extending between the end edges 52 and 54 of the second pad 24. The lines 60 are spaced from the side edges 48 and 50 of the second pad 24 throughout the length of the lines 60, and are preferably spaced from the side edges 48 and 50 of the second pad 24 approximately ½ inch in the crotch region of the second pad 24. The second pad 24 has relatively uncompressed areas similar to the first pad 22 adjacent the lines 60. The lines 60 may be formed by embossing the second pad 24 by suitable rollers either in the presence or absence of water, with the presence of water facilitating compression of the lines 60.

In accordance with the present invention, the lines 60 promote spreading of fluid adjacent the back sheet 14. The lines 60 cause spreading of fluid into the waistband portions of the diaper 10 against the force of gravity in the relatively long second pad 24. Also, the lines 60 add strength to the crotch region of the pad assembly 12, and the pad might otherwise bulk up during use of the diaper 10. Also, the spacing of the lines 60 from the side edges 48 and 50 of the second pad 24 minimizes spreading of fluid past the sides of the pad which otherwise might cause passage of fluids back against the wearer. Further, the areas of the second pad 24 intermediate the lines 60 and the side edges 48 and 50 provide a soft cushion of the pad 24 in conjunction with use of the elastic members 56 and 58.

The foregoing detailed description is given for clearness of understanding only, and no unnecessary limitations should be understood therefrom, as modifications will be obvious to those skilled in the art.

What is claimed is:

1. A disposable diaper comprising, a fluid impervious back sheet, a fluid pervious front sheet, a first absorbent pad adjacent the front sheet and comprising a loosely formed fibrous mass, and a separate second absorbent pad between the first pad and the back sheet, the second pad comprising a mass of fibers having compressed regions extending throughout a substantial part of the second pad and having relatively uncompressed areas adjacent the regions, said regions being spaced from opposed side edges of the second pad.

2. The diaper of claim 1 wherein the regions comprise lines of embossing.

3. The diaper of claim 1 wherein the regions are spaced approximately ½ inch from the side edges of the second pad in the crotch region of the second pad.

4. The diaper of claim 1 wherein the regions comprise a plurality of generally parallel lines extending at least substantially between opposed end edges of the second pad.

5. The diaper of claim 1 including a pair of elastic members located adjacent the side edges of the second pad in at least the crotch region of the second pad.

6. The diaper of claim 1 wherein the first and second pads have cut-outs in the crotch region of the pads.

7. A disposable diaper comprising, a fluid impervious back sheet, a fluid pervious front sheet, a first absorbent pad adjacent the front sheet and comprising a loosely formed fibrous mass, and a separate second absorbent pad between the first pad and the back sheet, the second pad comprising a mass of fibers having a plurality of generally parallel compressed regions extending at least substantially between opposed end edges of the second pad.

8. The diaper of claim 7 wherein the regions extend completely between the end edges of the second pad.

9. The diaper of claim 7 wherein the regions comprise lines of embossing.

10. The diaper of claim 7 wherein the regions are spaced from side edges of the second pad.

11. The diaper of claim 7 including a pair of elastic members located adjacent the side edges of the second pad in at least the crotch region of the second pad.

12. The diaper of claim 7 wherein the first and second pads have cut-outs in the crotch region of the pads.

13. The diaper of claim 1 wherein the compressed regions define recesses spaced from both a lower and upper surface of the second pad.

14. The diaper of claim 7 wherein the compressed regions define recesses spaced from both a lower and upper surface of the second pad.

* * * * *